(12) United States Patent
Pan et al.

(10) Patent No.: US 11,307,088 B2
(45) Date of Patent: Apr. 19, 2022

(54) OPTICAL TOMOGRAPHY IMAGING SYSTEM AND IMAGING METHOD FOR GENERATING A RECONSTRUCTED IMAGE ACCORDING TO PLURAL DISASSEMBLED SINE WAVES

(71) Applicants: National Central University, Taoyuan (TW); Huan-Cheng Chang, Taoyuan (TW)

(72) Inventors: Min-Chun Pan, Taoyuan (TW); Ya-Fen Hsu, Taoyuan (TW); Yan-Yang Hsu, Taoyuan (TW)

(73) Assignees: National Central University, Taoyuan (TW); Huan-Cheng Chang, Taoyuan (TW)

( * ) Notice: Subject to any disclaimer, the term of this patent is extended or adjusted under 35 U.S.C. 154(b) by 397 days.

(21) Appl. No.: 16/698,919

(22) Filed: Nov. 27, 2019

(65) Prior Publication Data
US 2021/0156738 A1 May 27, 2021

(30) Foreign Application Priority Data
Nov. 21, 2019 (TW) ................................. 108142399

(51) Int. Cl.
*G06T 11/00* (2006.01)
*G01J 1/44* (2006.01)
*A61B 5/00* (2006.01)

(52) U.S. Cl.
CPC .............. *G01J 1/44* (2013.01); *G06T 11/003* (2013.01); *A61B 5/0073* (2013.01); *G01J 2001/4413* (2013.01); *G01J 2001/4453* (2013.01)

(58) Field of Classification Search
CPC ........ A61B 5/72; G01J 1/44; G01J 2001/444; G06T 11/003; G06T 11/005; G06T 11/008
(Continued)

(56) References Cited

U.S. PATENT DOCUMENTS 6,472,668 B1 * 10/2002 Griesmer .............. G01T 1/1644
250/338.4

FOREIGN PATENT DOCUMENTS

| CN | 100403985 C | 7/2008 |
|---|---|---|
| CN | 108027229 A | 5/2018 |

(Continued)

OTHER PUBLICATIONS

Gulsen, G. et al., "Design and implementation of a multifrequency near-infrared diffuse optical tomography system," Journal of Biomedical Optics, 11(1), 10 pages, (2006).
(Continued)

*Primary Examiner* — Que Tan Le
(74) *Attorney, Agent, or Firm* — CKC & Partners Co., LLC

(57) ABSTRACT

An optical tomography imaging system includes a signal generator, at least one light emitter, at least one light receiver, a signal processor, and an image processor. The signal generator is configured to generate a periodic signal and a reference signal. The light emitter is configured to be activated by the periodic signal to generate an optical signal passing through an object under test. The light receiver is configured to receive and convert the optical signal passing through the object under test into an electrical signal. The signal processor is configured to generate a comparison signal according to the electrical signal and the reference signal. The image processor is configured to acquire a plurality of disassembled sine waves from the comparison
(Continued)

signal and generate a reconstructed image according to the disassembled sine waves.

10 Claims, 3 Drawing Sheets

(58) Field of Classification Search
USPC .......................................... 250/208.1, 214 R
See application file for complete search history.

(56) References Cited

FOREIGN PATENT DOCUMENTS

| | | |
|---|---|---|
| CN | 108366753 B | 6/2019 |
| TW | 201803521 A | 2/2018 |

OTHER PUBLICATIONS

Gulsen, G. et al., "Combined Diffuse Optical Tomography (DOT) and MRI System for Cancer Imaging in Small Animals" Technology in Cancer Research & Treatment, vol. 5, No. 4, pp. 351-363, (2006).

\* cited by examiner

OPTICAL TOMOGRAPHY IMAGING SYSTEM AND IMAGING METHOD FOR GENERATING A RECONSTRUCTED IMAGE ACCORDING TO PLURAL DISASSEMBLED SINE WAVES

CROSS-REFERENCE TO RELATED APPLICATION

This application claims priority to Taiwan Application Serial Number 108142399, filed Nov. 21, 2019, which is herein incorporated by reference in its entirety.

BACKGROUND

Field of Invention

The present disclosure relates to an imaging system and an imaging method, and more particularly, to an imaging system and an imaging method used for optical tomography scanning.

Description of Related Art

The statements in this section merely provide background information related to the present disclosure and do not necessarily constitute prior art.

Cancer has gradually become one of the top causes of human death in modern society due to changes about diet, pollution, and lifestyle.

Near Infrared Diffuse Optical Tomography (NIR DOT) is a novel functional technique of imaging. However, since the received optical information of each scan is insufficient, not only numerous times of scans are needed but also much time period is required. Moreover, the accuracy of NIR DOT would decline due to cross talk resulting from scattering coefficient and absorption coefficient of tissues.

Accordingly, how to provide an optical tomography imaging system to solve the aforementioned problems becomes an important issue to be solved by those in the industry.

SUMMARY

An aspect of the disclosure is to provide an optical tomography imaging system which can effectively solve the aforementioned problems.

According to some embodiments of the present disclosure, an optical tomography imaging system includes a signal generator, at least one light emitter, at least one light receiver, a signal processor, and an image processor. The signal generator is configured to generate a periodic signal and a reference signal. The light emitter is configured to be activated by the periodic signal to generate an optical signal passing through an object under test. The light receiver is configured to receive and convert the optical signal passing through the object under test into an electrical signal. The signal processor is configured to generate a comparison signal according to the electrical signal and the reference signal. The image processor is configured to acquire a plurality of disassembled sine waves from the comparison signal and generate a reconstructed image according to the disassembled sine waves.

In some embodiments of the disclosure, the light receiver comprises a photomultiplier tube and an amplifier, and the electrical signal is a voltage signal.

In some embodiments of the disclosure, the signal processor comprises a mixer configured to generate the comparison signal according to the voltage signal and the reference signal and a low-pass filter configured to remove high-frequency signals of the comparison signal.

In some embodiments of the disclosure, the periodic signal comprises a plurality of superimposition sine waves.

In some embodiments of the disclosure, the image processor comprises a signal capturing component configured to capture the disassembled sine waves of the comparison signal.

According to some embodiments of the present disclosure, an imaging method is provided. The imaging method includes: activating a light emitter by a period signal to generate an optical signal passing through an object under test; receiving and converting the optical signal passing through an object under test into an electrical signal; generating a comparison signal according to the electrical signal and the reference signal; acquiring a plurality of disassembled sine waves from the comparison signal; and generating a reconstructed image according to the disassembled sine waves.

In some embodiments of the disclosure, the electrical signal is a voltage signal.

In some embodiments of the disclosure, the imaging method further includes: generating the comparison signal according to the voltage signal and the reference signal and removing high-frequency signals of the comparison signal.

In some embodiments of the disclosure, the periodic signal includes a plurality of superimposition sine waves.

In some embodiments of the disclosure, the imaging method further includes: capturing the disassembled sine waves of the comparison signal.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
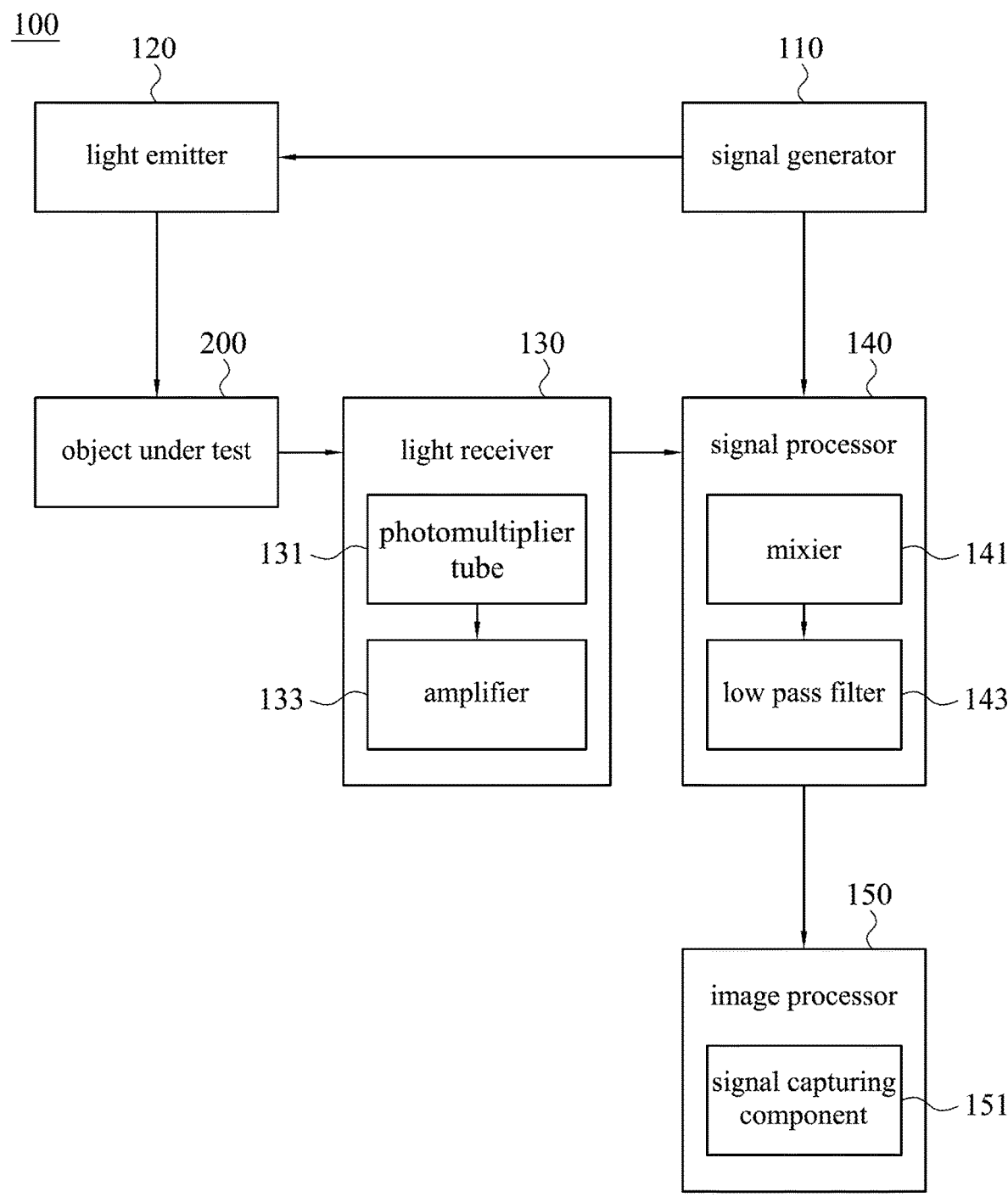
FIG. 1 is a functional block diagram of an optical tomography imaging system according to an embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

In various embodiments, description is made with reference to figures. However, certain embodiments may be practiced without one or more of these specific details, or in combination with other known methods and configurations. In the following description, numerous specific details are set forth, such as specific configurations, dimensions and processes, etc., in order to provide a thorough understanding of the present disclosure. Reference throughout this specification to "one embodiment," "an embodiment", "some embodiments" or the like means that a particular feature, structure, configuration, or characteristic described in connection with the embodiment is included in at least one embodiment of the disclosure. Thus, the appearances of the phrase "in one embodiment," "in an embodiment", "in some embodiments" or the like in various places throughout this specification are not necessarily referring to the same embodiment of the disclosure. Furthermore, the particular features, structures, configurations, or characteristics may be combined in any suitable manner in one or more embodiments.

Reference is made to FIG. 1. FIG. 1 illustrates a functional block diagram according to an embodiment of the present disclosure. In some embodiments, the optical tomography imaging system 100 includes a signal generator 110, at least one light emitter 120, at least one light receiver 130, a signal processor 140, and an image processor 150. The signal generator 110 is configured to generate a periodic signal and a reference signal. The light emitter 120 is configured to be activated by the periodic signal to generate an optical signal passing through an object under test 200. The light receiver 130 is configured to receive and convert the optical signal passing through the object under test into an electrical signal. The signal processor 140 is configured to generate a comparison signal according to the electrical signal and the reference signal. The image processor 150 is configured to acquire a plurality of disassembled sine waves from the comparison signal and generate a reconstructed image according to the disassembled sine waves.

Reference is made to FIG. 1. In some embodiments of the present disclosure, the signal generator 110 generates a periodic signal to activate the light emitter 120 to generate an optical signal. The periodic signal substantially includes a plurality of superimposition sine waves (that is, the periodic signals can be substantially disassembled into a plurality of superimposition sine waves). The periodic signal can be a square wave, a triangle wave, or a resultant wave. Specifically, the periodic signal includes a plurality of superimposition sine waves with different frequencies. For example, when the periodic signal is a square wave, the square wave essentially includes three and more superimposition sine waves (that is, the periodic signal can be appropriately disassembled into three superimposition sine waves). The frequencies of the first three superimposition sine waves can have a multiple relationship of 1, 3, and 5. That is, if the periodic signal is a 50 MHz square wave, the periodic signal substantially includes 50 MHz, 150 MHz, 250 MHz, and more superimposition sine waves.

Reference is made to FIG. 1. In some embodiments of the present disclosure, the periodic signal activates the light emitter 120 to generate an optical signal passing through an object under test. Specifically, the light emitter 120 includes a light-emitting diode (LED), and the light-emitting diode is activated by the periodic signal to emit an optical signal. The optical signal can be a near-infrared (NIR) optical signal. The object under test 200 may be a human body, such as a breast.

Reference is made to FIG. 1. In some embodiments of the present disclosure, the light receiver 130 is configured to receive and convert the optical signal passing through the object under test 200 into an electrical signal. The light receiver 130 includes a photomultiplier tube 131 (PMT) and an amplifier 133. Specifically, the photomultiplier tube 131 receives and converts the optical signal passing through the object under test 200 into a current signal. The amplifier 133 is configured to convert the current signal into a voltage signal. Specifically, the amplifier 133 is a preamplifier, and the voltage signal is more suitable for the image processor 150 to generate a reconstructed image.

In some embodiments, the optical tomography imaging system 100 may include a plurality of light receivers 130. That is, the optical tomography imaging system 100 may include a plurality of photomultiplier tubes 131. The plurality of photomultiplier tubes 131 are configured to respectively receive the optical signals from the light emitter 120 which is activated by the periodic signal, and so as to receive optical signals more efficiently. The photomultiplier tubes 131 are configured to respectively receive the optical signals of different frequencies, thereby making the light receiving efficiency of the photomultiplier tubes better.

For example, while the periodic signal is a 50 MHz square wave, it substantial includes 50 MHz, 150 MHz, and 250 MHz superimposition sine waves. Three photomultiplier tubes 131 are configured to respectively receive the optical signals from the light emitter 120 activated by the 50 MHz, 150 MHz, and 250 MHz superimposition sine waves, and the optical signals are also converted into three current signals by the three photomultiplier tubes 131. Receiving efficiency of three photomultiplier tubes 131 would be better than one regarding receiving the optical signals which are emitted by the light emitters 120 activated by the 50 MHz, 150 MHz, and 250 MHz superimposition sine waves. In some specific embodiments of the present disclosure, the optical tomography imaging system 100 may include one, two, or three photomultiplier tubes 131. Depending on the necessaries of users, more photomultiplier tubes 131 may be configured in the optical tomography imaging system 100, and the number of photomultiplier tubes 131 is not limited in the present disclosure.

Reference is made to FIG. 1. In some embodiments of the present disclosure, the signal processor 140 is configured to generate a comparison signal according to the electrical signal and the reference signal. The signal processor 140 includes a mixer 141 and a low pass filter 143. Specifically, the mixer 141 is configured to generate the comparison signal according to the voltage signal and the reference signal. The low pass filter 143 is configured to remove noise of the comparison signal, so that the image processor 150 can acquire only the necessary portion of the comparison signal. That is, with the configuration of the low pass filter 143, the image processor 150 can avoid the interference of noise.

Reference is made to FIG. 1. In some embodiments of the present disclosure, the comparison signal substantially includes a plurality of disassembled sine waves. That is, the comparison signal may mainly be disassembled into a plurality of disassembled sine waves. The image processor 150 is configured to acquire a plurality of disassembled sine waves of the comparison signal and generate a reconstructed image according to the disassembled sine waves. By exploiting the disassembled sine waves to reconstruct images, tomographic images with a higher quality can be obtained.

Specifically, in the process of generating the comparison signal by the mixer 141 according to the voltage signal and the reference signal, the mixer 141 generates a high-frequency signal based on the sum of the voltage signal and the reference signal, and the mixer 141 also generates a low-frequency signal based on the difference between the voltage signal and the reference signal.

Further, the comparison signal substantially includes a plurality of disassembled sine waves, and the comparison signal can be disassembled into a high-frequency signal and a low-frequency signal. Each of the disassembled sine waves of the comparison signal can also be disassembled into a high-frequency disassembled sine wave and a low-frequency disassembled sine wave. The low-pass filter 143 removes the high-frequency disassembled sine waves, thereby preventing the high-frequency disassembled sine waves from affecting the image processor 150 and obtaining optical tomographic images with a higher quality.

Reference is made to FIG. 1. In some embodiments of the present disclosure, the image processor 150 includes a signal capturing component 151 which is configured to capture the disassembled sine waves of the comparison signal. Specifically, the signal capturing component 151 is a data acquisition module (DAQ). The image processor 150 captures low-frequency disassembled sine waves through the data acquisition module to obtain optical tomographic images with a higher quality.

Figure 2:
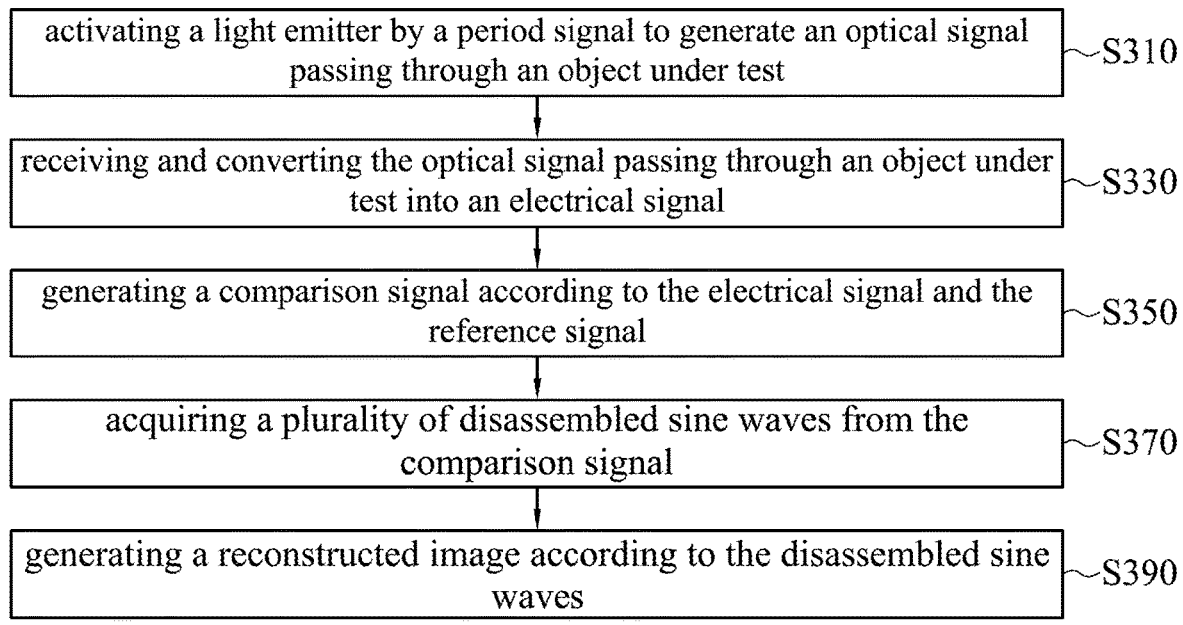
FIG. 2 is a flow diagram of an imaging method according to an embodiment of the present disclosure.
Figure 3:
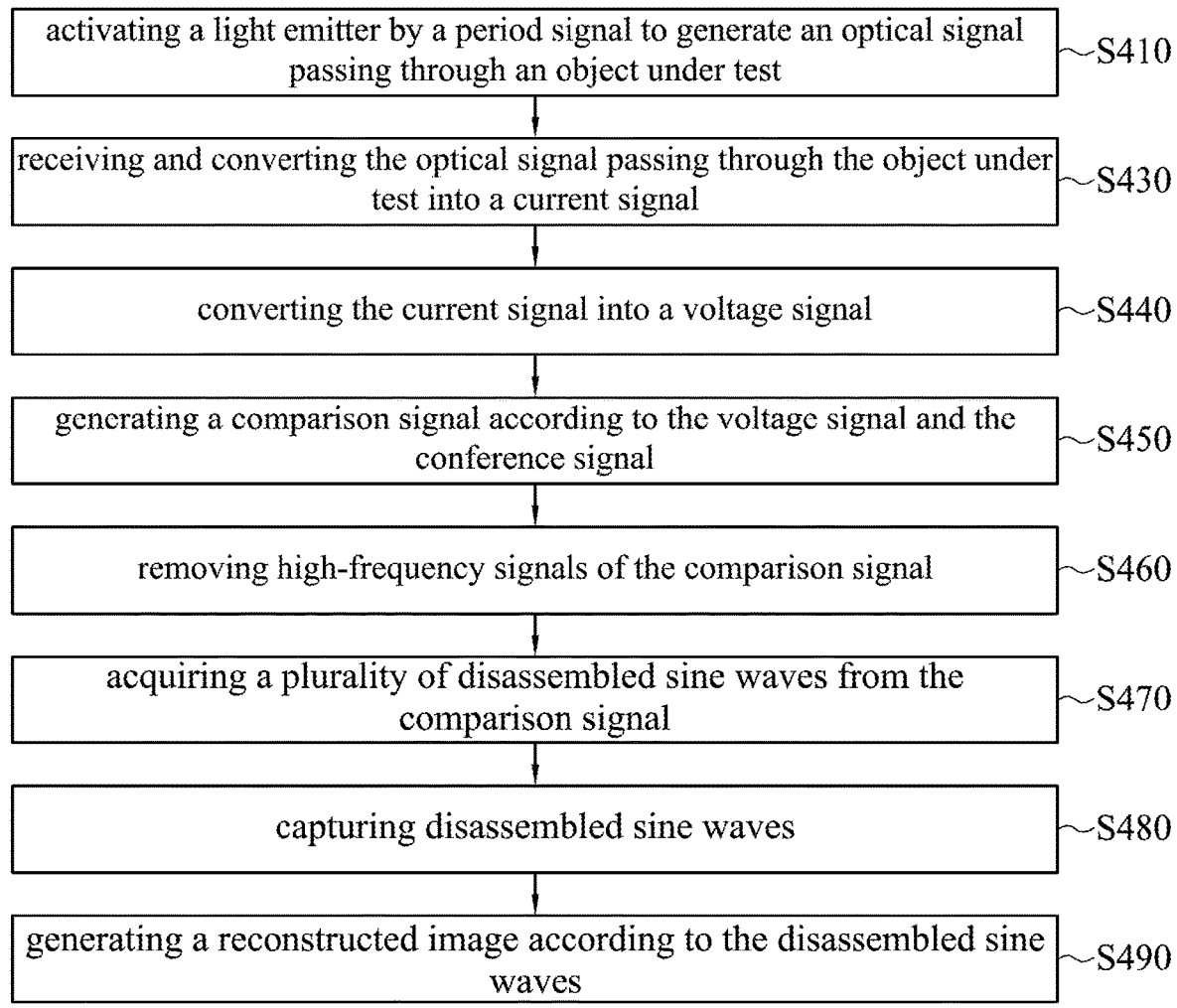
FIG. 3 is a flow diagram of an imaging method according to another embodiment of the present disclosure.

Reference is made to FIG. 2. The disclosure also provides an imaging method 300 including the following steps. The imaging method 300 begins with step S310: activating a light emitter by a period signal to generate an optical signal passing through an object under test. The imaging method 300 continues with step S330: receiving and converting the optical signal passing through an object under test into an electrical signal. The imaging method 300 continues with step S350: generating a comparison signal according to the electrical signal and the reference signal. The imaging method 300 continues with step S370: acquiring a plurality of disassembled sine waves from the comparison signal. Finally, the imaging method continues with step S390: generating a reconstructed image according to the disassembled sine waves.

In step S310, the light emitter can include a light-emitting diode (LED). The object under test may be a human body such as a breast. Moreover, the periodic signal of step S310 substantially includes a plurality of superimposition sine waves (that is, the periodic signals can be substantially disassembled into a plurality of superimposition sine waves). A plurality of superimposition sine waves can activate the light emitter to generate more light information, thereby achieving better imaging results.

In step S330, at least one light receiver receives and converts the optical signal passing through the object under test into an electrical signal. The light receiver includes a photomultiplier tube (PMT) and an amplifier. The photomultiplier tube receives and converts the optical signal passing through the object under test into a current signal. The amplifier is configured to convert the current signal into a voltage signal. Therefore, the electrical signal is a voltage signal. In fact, a plurality of light receivers can be configured to respectively receive the optical signals from the light emitter which is activated by the periodic signal, thereby increasing sensitivity of receiving optical signals. Users can actually adjust the number of photomultiplier tubes based on their requirements, and the disclosure is not limited thereto.

In step S350, the mixer 141 as shown in FIG. 1 can be used to generate a comparison signal according to the electrical signal and the reference signal.

In step S370, the comparison signal substantially includes a plurality of disassembled sine waves. That is, the comparison signal may be mainly disassembled into a plurality of disassembled sine waves.

In step S390, the image processor 150 as shown in FIG. 1 can be used to generate a reconstructed image according to the disassembled sine waves. By exploiting the disassembled sine waves to generate a reconstructed image, tomographic images with a higher quality can be obtained.

Reference is made to FIG. 2. The disclosure also provides an imaging method 400 and the following are the difference between the imaging method 300 and the imaging method 400. Compared with step S330, step S430 is receiving and converting the optical signal passing through the object under test 200 into a current signal. The imaging method 400 further includes step S440 which is converting the current signal into a voltage signal. Compare with step S350, step S450 is generating a comparison signal according to the voltage signal and the conference signal. The imaging method 400 further includes step S460 which is removing high-frequency signals of the comparison signal. The imaging method 400 further includes step S480 which is capturing disassembled sine waves. Since the rest steps of the imaging method 400 are basically the same as the steps of imaging method 300, the redundant details about the same steps are abridged.

In step S440, the amplifier 133 as shown in FIG. 1 can be used to convert the current signal into a voltage signal.

In step S450, the mixer 141 as shown in FIG. 1 can be used to generate a comparison signal according to the voltage signal and the reference signal. The mixer generates a high-frequency signal based on the sum of the voltage signal and the reference signal, and the mixer also generates a low-frequency signal based on the difference between the voltage signal and the reference signal, thereby the comparison signal including the low-frequency signal and the high-frequency signal.

In step S460, the low pass filter 143 as shown in FIG. 1 can be used to remove the high-frequency signals of the comparison signal. The comparison signal substantially includes a plurality of disassembled sine waves, and the comparison signal also includes the high-frequency signal and the low-frequency signal. Therefore, the disassembled sine waves include high-frequency disassembled sine waves and low-frequency disassembled sine waves. The low pass filter is configured to remove and prevent the high-frequency disassembled sine waves from interfering in order to obtain reconstructed images with a higher quality.

In step S480, the signal capturing component 151 as shown in FIG. 1 can be used to capture the disassembled sine waves, wherein the signal capturing component can be a data acquisition module.

In summary, in some of the above embodiments, periodic signals generated by the signal generator include a plurality of superimposition sine waves. The periodic signal can be used to activate the light emitter during tomographic scanning. Numerous times of light information can be obtained about the object under test after optical signals passing through the object under test, thereby shortening the time period of tomographic scanning. Specifically, a plurality of disassembled sine waves can be obtained from the comparison signal, and users can obtain tomographic images with a higher quality by using the disassembled sine waves to reconstruct images.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the method and the structure of the present disclosure without departing from the scope or spirit of the disclosure. In view of the foregoing, it is intended that the present disclosure cover modifications and variations of this disclosure provided they fall within the scope of the following claims.

What is claimed is:

1. An optical tomography imaging system, comprising:
   a signal generator configured to generate a periodic signal and a reference signal;

at least one light emitter configured to be activated by the periodic signal to generate an optical signal passing through an object under test;

at least one light receiver configured to receive and convert the optical signal passing through the object under test into an electrical signal;

a signal processor configured to generate a comparison signal according to the electrical signal and the reference signal; and an image processor configured to acquire a plurality of disassembled sine waves from the comparison signal and generate a reconstructed image according to the disassembled sine waves.

2. The optical tomography imaging system of claim 1, wherein the light receiver comprises a photomultiplier tube and an amplifier, and the electrical signal is a voltage signal.

3. The optical tomography imaging system of claim 2, wherein the signal processor comprises a mixer configured to generate the comparison signal according to the voltage signal and the reference signal and a low-pass filter configured to remove high-frequency signals of the comparison signal.

4. The optical tomography imaging system of claim 1, wherein the periodic signal comprises a plurality of superimposition sine waves.

5. The optical tomography imaging system of claim 1, wherein the image processor comprises a signal capturing component configured to capture the disassembled sine waves of the comparison signal.

6. An imaging method, comprising:

activating a light emitter by a period signal to generate an optical signal passing through an object under test;

receiving and converting the optical signal passing through an object under test into an electrical signal;

generating a comparison signal according to the electrical signal and a reference signal;

acquiring a plurality of disassembled sine waves from the comparison signal; and generating a reconstructed image according to the disassembled sine waves.

7. The imaging method of claim 6, wherein the electrical signal is a voltage signal.

8. The imaging method of claim 7, further comprising:

generating the comparison signal according to the voltage signal and the reference signal; and removing high-frequency signals of the comparison signal.

9. The imaging method of claim 6, wherein the periodic signal comprises a plurality of superimposition sine waves.

10. The imaging method of claim 6, further comprising:

capturing the disassembled sine waves of the comparison signal.

* * * * *